(12) United States Patent
Pinel et al.

(10) Patent No.: US 7,404,948 B2
(45) Date of Patent: Jul. 29, 2008

(54) PEPTIDIC CONJUGATES FOR ALOPECIA PREVENTION AND TREATMENT

(75) Inventors: Anne-Marie Pinel, Toulouse (FR); Michel Hocquaux, Paris (FR)

(73) Assignee: Institut Europeen de Biologie Cellulaire, Ramonville St Agne (FR)

( * ) Notice: Subject to any disclaimer, the term of this patent is extended or adjusted under 35 U.S.C. 154(b) by 0 days.

(21) Appl. No.: 10/565,009

(22) PCT Filed: Jul. 16, 2004

(86) PCT No.: PCT/FR2004/001882

§ 371 (c)(1), (2), (4) Date: Jan. 18, 2006

(87) PCT Pub. No.: WO2005/010027

PCT Pub. Date: Feb. 3, 2005

(65) Prior Publication Data

US 2007/0014747 A1    Jan. 18, 2007

(30) Foreign Application Priority Data

Jul. 18, 2003    (FR) .................................. 03 08797

(51) Int. Cl.
*A61K 38/06* (2006.01)
*A61K 38/07* (2006.01)
*A61K 38/08* (2006.01)
*A61K 8/64* (2006.01)

(52) U.S. Cl. .................. 424/70.14; 514/15; 514/16; 514/17; 514/18; 530/327; 530/328; 530/329; 530/330; 530/331

(58) Field of Classification Search .................. 530/300
See application file for complete search history.

(56) References Cited

U.S. PATENT DOCUMENTS

| 5,017,368 | A | 5/1991 | Sugiyama et al. |
|---|---|---|---|
| 5,135,913 | A | 8/1992 | Pickart |
| 5,573,911 | A | 11/1996 | Victor et al. |
| 5,998,579 | A | 12/1999 | Koshida |
| 6,001,812 | A | 12/1999 | Mahe |
| 6,211,155 | B1 | 4/2001 | Dussourd et al. |
| 6,372,890 | B1 | 4/2002 | Koshida |
| 6,498,243 | B1 | 12/2002 | Koshida |
| 2004/0022838 | A1 | 2/2004 | Holick |

FOREIGN PATENT DOCUMENTS

| DE | 196 08 229 A | 9/1997 |
|---|---|---|
| EP | 0293837 A2 | 12/1988 |
| EP | 0837 129 A1 | 4/1998 |
| EP | 1008603 A1 | 6/2000 |
| EP | 0869969 B1 | 3/2003 |
| EP | 0861266 B1 | 4/2003 |
| FR | 2733421 A1 | 10/1996 |
| WO | WO-97/18235 | 5/1997 |
| WO | WO-97/18239 A | 5/1997 |
| WO | WO-01/98348 A2 | 12/2001 |

OTHER PUBLICATIONS

Alopecia from the Merck manual.*
Leshin L, Dermatologi DIsorders in Down Syndrome form www.ds-health.com/derm.htm, 2001.*
Hair Loss-Hair Loss Treatment for Male Pattern Baldness from www. webmeds.us/hair-loss.html.*
Hair Loss-Better Health Channel from betterhealthchannel.vic.gov.au/bhcv2/bhcarticles.nsf/pages/Hair_loss?Open.*
Types of Hair Loss from www.pennhealth.com/hairtransplant/types.html.*
Frequently Asked Questions from www.naaf.org/requestinfo/faq.asp.*
Tosti, A. et al., Thymopentin Treatment of Severe Alopecia Areata, vol. 177, No. 3, pp. 170-174 (1988).
Biologie Du Cheveu Et Du Cuir Chevelu, pp. 14-17, 1999.
P. Bouhanna, et al., Anatomie Et Methodes D'Exploration, pp. 51-55, 1999.
Philpott, M.P., et al., Human Hair Growth in Vitro: a model for the study of hair follicle biology, Journal of Dematological Science 7 (Suppl.) (1994), pp. 55-72.

* cited by examiner

*Primary Examiner*—Anish Gupta
*Assistant Examiner*—Julie Ha
(74) *Attorney, Agent, or Firm*—Birch, Stewart, Kolasch & Birch, LLP

(57) ABSTRACT

The invention relates to novel peptidic conjugates containing a Gly-His-Lys sequence and used for dermatology or cosmetology for stimulating hair growth or stopping hair fall.

14 Claims, No Drawings

SEQUENCE LISTING

<160> NUMBER OF SEQ ID NOS: 12

<210> SEQ ID NO 1
<211> LENGTH: 11
<212> TYPE: PRT
<213> ORGANISM: Artificial sequence
<220> FEATURE:
<223> OTHER INFORMATION: Synthetic Peptide
<220> FEATURE:
<221> NAME/KEY: misc_feature
<222> LOCATION: (1)..(3)
<223> OTHER INFORMATION: Xaa can be Glu-Gln-Arg, Arg-Lys, Arg-Lys-Asp
      sequences or Arg amino acid or a bond and up to
      3 residues may be present or absent
<220> FEATURE:
<221> NAME/KEY: misc_feature
<222> LOCATION: (7)..(11)
<223> OTHER INFORMATION: Xaa can be Tyr-Val-Gln-Leu-Tyr-Amide, Leu-DOPA
      sequences, the amino acids Dopa amide or HomoPhe amide and up to 4
      residues may be present or absent

<400> SEQUENCE: 1

Xaa Xaa Xaa Lys Asp Val Xaa Xaa Xaa Xaa Xaa
1               5                   10

```
<210> SEQ ID NO 2
<211> LENGTH: 11
<212> TYPE: PRT
<213> ORGANISM: Artificial sequence
<220> FEATURE:
<223> OTHER INFORMATION: Synthetic Peptide
<220> FEATURE:
<221> NAME/KEY: misc_feature
<222> LOCATION: (1)..(3)
<223> OTHER INFORMATION: Xaa can be Gly-Gln-Gln or Glu-Gln sequences and
      up to 1 residue may be present or absent
<220> FEATURE:
<221> NAME/KEY: misc_feature
<222> LOCATION: (7)..(11)
<223> OTHER INFORMATION: Xaa can be Tyr-Val-Gln-Leu-Tyr-Amide, Leu-DOPA,
      Val-Tyr, Val-Tyr-amide sequences, or the amino acids Tyr, Tyr
      amide, Dopa amide or HomoPhe amide amide and up to 4 residues may
      be present or absent

<400> SEQUENCE: 2

Xaa Xaa Xaa Lys Asp Val Xaa Xaa Xaa Xaa Xaa
1               5                   10

<210> SEQ ID NO 3
<211> LENGTH: 11
<212> TYPE: PRT
<213> ORGANISM: Artificial sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: BLOCKED
<220> FEATURE:
<221> NAME/KEY: misc_feature
<222> LOCATION: (1)..(3)
<223> OTHER INFORMATION: Xaa can be Glu-Gln-Arg, Arg-Lys, Arg-Lys-Asp
      sequences or Arg amino acid or a bond and up to 3 residues may
      be present or absent
<220> FEATURE:
<221> NAME/KEY: misc_feature
<222> LOCATION: (7)..(11)
<223> OTHER INFORMATION: Xaa can be Tyr-Val-Gln-Leu-Tyr-Amide, Leu-DOPA
      sequences, the amino acids Dopa amide or HomoPhe amide and up to 4
      residues may be present or absent

<400> SEQUENCE: 3

Xaa Xaa Xaa Lys Asp Val Xaa Xaa Xaa Xaa Xaa
1               5                   10

<210> SEQ ID NO 4
<211> LENGTH: 11
<212> TYPE: PRT
<213> ORGANISM: Artificial sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: BLOCKED
<220> FEATURE:
<221> NAME/KEY: misc_feature
<222> LOCATION: (1)..(3)
<223> OTHER INFORMATION: Xaa can be Gly-Gln-Gln or Glu-Gln sequences and
      up to 1 residue may be present or absent
<220> FEATURE:
<221> NAME/KEY: misc_feature
<222> LOCATION: (7)..(11)
<223> OTHER INFORMATION: Xaa can be Tyr-Val-Gln-Leu-Tyr-Amide, Leu-DOPA,
      Val-Tyr, Val-Tyr-amide sequences, or the amino acids Tyr, Tyr
      amide, Dopa amide or HomoPhe amide and up to 4 residues
      may be present or absent
```

```
<400> SEQUENCE: 4

Xaa Xaa Xaa Lys Asp Val Xaa Xaa Xaa Xaa
1               5                   10

<210> SEQ ID NO 5
<211> LENGTH: 5
<212> TYPE: PRT
<213> ORGANISM: Artificial sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: BLOCKED
<220> FEATURE:
<221> NAME/KEY: MOD_RES
<222> LOCATION: (5)..(5)
<223> OTHER INFORMATION: AMIDATION
<220> FEATURE:
<221> NAME/KEY: misc_feature
<222> LOCATION: (5)..(5)
<223> OTHER INFORMATION: Xaa = homophenylalanine amide.

<400> SEQUENCE: 5

Arg Lys Asp Val Xaa
1               5

<210> SEQ ID NO 6
<211> LENGTH: 4
<212> TYPE: PRT
<213> ORGANISM: Artificial sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: BLOCKED
<220> FEATURE:
<221> NAME/KEY: MOD_RES
<222> LOCATION: (4)..(4)
<223> OTHER INFORMATION: AMIDATION
<220> FEATURE:
<221> NAME/KEY: misc_feature
<222> LOCATION: (4)..(4)
<223> OTHER INFORMATION: Xaa = dihydrophenylalanine amide.

<400> SEQUENCE: 6

Lys Asp Val Xaa
1

<210> SEQ ID NO 7
<211> LENGTH: 5
<212> TYPE: PRT
<213> ORGANISM: Artificial sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: BLOCKED
<220> FEATURE:
<221> NAME/KEY: MOD_RES
<222> LOCATION: (5)..(5)
<223> OTHER INFORMATION: AMIDATION
<220> FEATURE:
<221> NAME/KEY: misc_feature
<222> LOCATION: (5)..(5)
<223> OTHER INFORMATION: Xaa = dihydrophenylalaline amide.

<400> SEQUENCE: 7

Arg Lys Asp Val Xaa
1               5
```

```
<210> SEQ ID NO 8
<211> LENGTH: 6
<212> TYPE: PRT
<213> ORGANISM: Artificial sequence
<220> FEATURE:
<223> OTHER INFORMATION: Synthetic Peptide
<220> FEATURE:
<221> NAME/KEY: misc_feature
<222> LOCATION: (1)..(3)
<223> OTHER INFORMATION: Xaa is Lys or MeLys and up to two residues may
      be present or absent

<400> SEQUENCE: 8

Xaa Xaa Xaa Gly His Lys
1               5

<210> SEQ ID NO 9
<211> LENGTH: 6
<212> TYPE: PRT
<213> ORGANISM: Artificial sequence
<220> FEATURE:
<223> OTHER INFORMATION: Synthetic Peptide
<220> FEATURE:
<221> NAME/KEY: misc_feature
<222> LOCATION: (1)..(3)
<223> OTHER INFORMATION: Xaa is Lys or MeLys and up to two residues may
      be present or absent
<220> FEATURE:
<221> NAME/KEY: MOD_RES
<222> LOCATION: (6)..(6)
<223> OTHER INFORMATION: AMIDATION

<400> SEQUENCE: 9

Xaa Xaa Xaa Gly His Lys
1               5

<210> SEQ ID NO 10
<211> LENGTH: 6
<212> TYPE: PRT
<213> ORGANISM: Artificial sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: BLOCKED
<220> FEATURE:
<221> NAME/KEY: misc_feature
<222> LOCATION: (1)..(3)
<223> OTHER INFORMATION: Xaa is Lys, MeLys, or a bond and up to three
      residues may be present or absent

<400> SEQUENCE: 10

Xaa Xaa Xaa Gly His Lys
1               5

<210> SEQ ID NO 11
<211> LENGTH: 6
<212> TYPE: PRT
<213> ORGANISM: Artificial sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: BLOCKED
<220> FEATURE:
<221> NAME/KEY: misc_feature
<222> LOCATION: (1)..(3)
<223> OTHER INFORMATION: Xaa is Lys, MeLys, or a bond and up to three
      residues may be present or absent
```

```
-continued

<220> FEATURE:
<221> NAME/KEY: MOD_RES
<222> LOCATION: (6)..(6)
<223> OTHER INFORMATION: AMIDATION

<400> SEQUENCE: 11

Xaa Xaa Xaa Gly His Lys
1               5

<210> SEQ ID NO 12
<211> LENGTH: 5
<212> TYPE: PRT
<213> ORGANISM: Artificial Sequence
<220> FEATURE:
<223> OTHER INFORMATION: Synthetic peptide

<400> SEQUENCE: 12

Tyr Val Gln Leu Tyr
1               5
```

PEPTIDIC CONJUGATES FOR ALOPECIA PREVENTION AND TREATMENT

The present invention has as its aim novel peptide conjugates containing the sequence Lys-Asp-Val, useful in dermatology or beauty care, in particular to stimulate hair growth or to slow hair loss.

Throughout an individual's lifetime, hair growth and its renewal are determined by the activity of hair follicles. The follicles undergo a regular cycle consisting of three phases—anagen, catagen, and telogen—each of which is characterized by quite distinct molecular and cellular mechanisms:

During the approximately three-year anagen phase, the cells of the dermal papilla "send" signals to the stem cells present in the bulb. The relevant cells receiving these signals then migrate towards the hair follicle matrix, and are thus referred to as matrix cells. In this area, the cells of the dermal papilla emit additional signals which enable the matrix cells to initially proliferate and then to differentiate, which allows the hair shaft to lengthen. During this phase, the hair follicle migrates through the dermis and is, in anagen VI, anchored in the hypodermis in contact with adipose tissue.

The phase which follows, called catagen, is a short phase which lasts approximately three weeks, during which cells in the lower part of the hair follicle re-enter apoptosis, thus enabling degeneration of the hair follicle.

The remaining phase, called telogen, is a resting phase characterized by inactivity of the hair follicle for three months and the loss of hair before a new anagen phase begins.

Personal appearance being of paramount social importance today, hair loss is a genuine problem that is felt to be a social handicap by some. In men, the majority of cases are androgenic alopecia. This type of alopecia is due to a defect in the catabolism of androgens, more precisely of testosterone, at the level of the hair follicle, by the cells of the dermal papilla. Indeed, there is an accumulation of a metabolite of testosterone, DHT (a metabolite which is produced by the action of 5α-reductase on testosterone), at the level of the hair follicles. In a normal process, this compound is degraded and then eliminated in the urine. Currently, inhibitors of 5α-reductase are used in this type of alopecia to slow hair loss.

The current body of knowledge concerning hair and scalp biology, alopecias, scalp affections, and their treatment are collected in: "Hair and scalp pathology", P. Bouhanna and P. Reygagne, Editions Masson.

For many years, the cosmetics and pharmaceuticals industries have searched for substances that enable the abolition or the reduction of the effect of alopecia, in particular substances that induce or stimulate hair growth or that decrease hair loss.

A certain number of compounds are already used, such as minoxidil and finasteride.

Certain peptides are known for their stimulatory effect on hair growth, however no document reveals the peptides or peptide conjugates which are the aim of this invention.

The applicant has synthesized novel peptides and peptide conjugates containing the sequence Lys-Asp-Val capable of combating alopecia.

The present invention thus has as an aim a peptide corresponding to the formula (I)

W-Lys-Asp-Val-Z  (I)  (SEQ ID NO. 1-2)

or its peptide conjugate corresponding to the formula (II)

A-W-Lys-Asp-Val-Z  (II)  (SEQ ID NO. 3-4)

in which
A represents the radical corresponding to
  a monocarboxylic acid of general formula (III)

HOOC—R  (III)

in which
R represents a C1-C24 aliphatic radical, linear or branched, possibly substituted by a hydroxy group, capable of including one or more unsaturations, advantageously from 1 to 6 unsaturations,
  lipoic acid or its reduced form, dihydrolipoic acid, Nlipoyl-lysine, or retinoic acid,
and W represents
Glu-Gln-Arg, Arg-Lys, Arg-Lys-Asp, Arg or a bond,
when Z represents
Tyr-Val-Gln-Leu-Tyr-NH2 (SEQ ID NO: 12), Leu-DOPA, DOPA-NH2, or HomoPhe-NH2,
or W represents
Gly-Gln-Gln or Glu-Gln,
when Z represents
Tyr-Val-Gln-Leu-Tyr-NH2 (SEQ ID NO: 12), Leu-DOPA, Val-Tyr-OH, Val-Tyr-NH2,
TyrNH2, Tyr-OH, DOPA-NH2, or HomoPhe-NH2.

Advantageously, the peptide sequence is conjugated chemically or physically with the acids A. The peptides conjugated according to the invention are linked to these acids A in the form of salts, esters, or amides, the carboxylic acid fraction of the acid ensuring the bond.

The amino acids in the peptide of formula (I) can have a D, L, or DL configuration.

In other words, the formula (I) peptide conjugates can comprise one or more atoms of asymmetrical carbon. Thus, they can exist in the form of enantiomers or diastereomers. These enantiomers and diastereomers, as well as their mixtures, including racemic mixtures, are part of the invention.

The peptide conjugates of formula (II) are derivatives of low molecular weight which are obtained in the form of amides of the compound of formula (III).

Moreover, the peptides of formula (I) and the peptide conjugates of formula (II) can be coupled with zinc in salt form to form complexes.

Within the framework of the present invention, it is meant by:
  Lys, lysine,
  Asp, aspartic acid,
  Val, valine,
  Arg, arginine,
  Tyr, tyrosine,
  DOPA, dihydroxyphenylalanine,
  HomoPhe, homophenylalanine.

It is also specified that the peptide conjugates mentioned above, which are the object of the present invention, can be obtained in NH2-terminal form (in other words presenting an amide function) or in OH-terminal form (in other words presenting a carboxylic acid function).

Preferably, the acid of formula (III) is a polyunsaturated fatty acid, that is to say comprising from 1 to 6 unsaturations. Still more preferably, it is an omega-3 acid.

Among these omega-3 acids can be cited in particular α-linolenic acid, cervonic acid, timnodonic acid, and pinolenic acid.

Cervonic, timnodonic, and pinolenic acids are also known as 4,7,10,13,16,19-docosahexaenoic acid (DHA), 5,8,11,14,17-eicosapentaenoic acid (EPA), and 5,9,12-octadecatrienoic acid, respectively.

When A represents a monocarboxylic acid of general formula (III), it can be advantageously selected among acetic acid, myristic acid, palmitic acid, hydroxydecenoic and decenoic acids, and in particular, trans-10-hydroxy-Δ2-decenoic acid and trans-oxo-9-decene-2-oic acid.

Among the peptide conjugates of the invention the following peptide conjugates can be cited:

```
1- A-Arg-Lys-Asp-Val-DHomoPhe-NH2

2- A-Arg-Lys-Asp-Val-HomoPhe-NH2    (SEQ ID NO. 5)

3- A-Lys-Asp-Val-DOPA-NH2           (SEQ ID NO. 6)

4- A-DLys-Asp-Val-DOPA-NH2

5- A-Arg-Lys-Asp-Val-DOPA-NH2       (SEQ ID NO. 7)
```

The peptide conjugates for which A is selected among lipoic acid and acetic acid are particularly adapted within the framework of the present invention.

The peptide conjugates, which are the object of the present invention, can be obtained either by classic chemical synthesis or by enzymatic synthesis, according to methods known by those skilled in the art.

Peptides or their peptide conjugates can be administered for their cosmetic use via the topical route. They can also be used in food supplements, in other words in the nutraceutical industry, via the oral route.

The peptide conjugates according to the invention are preferentially administered via the topical route.

The present invention also has as an aim a peptide or a peptide conjugate according to the invention for use as a medicine, as well as the use of a peptide or a peptide conjugate according to the invention for the preparation of a compound intended for the preventive and curative treatment of alopecia.

According to another aspect, the present invention also has as an aim a cosmetic or dermatological compound that includes a peptide or a peptide conjugate according to the present invention, or a food supplement that includes a peptide or a peptide conjugate according to the present invention, possibly in association with a compound that improves hair growth such as defined below.

The cosmetic or dermatological compound can be applied advantageously to the entire scalp.

The cosmetic or dermatological compound can, for example, be presented in the form of a lotion, a medicated shampoo, a spray, a gel, or a medicated cream.

In the topical cosmetic compound; the peptide conjugate according to the invention can be present in a concentration ranging between $10^{-8}$ M and $10^{-3}$ M, preferably ranging between $10^{-7}$ M and $10^{-5}$ M.

Lastly, another aim of the present invention relates to a cosmetic treatment method to combat hair loss that includes the application on the scalp of a compound comprising a peptide or a peptide conjugate of the invention, alone or in association as described below, or comprising the administration via the oral route of a food supplement that includes a peptide or a peptide conjugate of the invention, alone or in association as described below.

It is possible to use, in association with the peptide conjugates according to the invention, compounds that also improve hair growth activity and that have already been described for this activity.

Among these compounds can be cited:
peptides that stimulate the production of native collagen and lead to a strengthening of the extracellular matrix,
minoxidil,
nicotinic acid esters,
anti-inflammatory agents, more particularly peptides with anti-inflammatory activity,
retinoic acid, its derivatives, and retinol,
5α-reductase inhibitors.

Among the compounds that also improve hair growth and can be associated with the peptide or peptide conjugate, the peptides that correspond to the general formula (I) can also be cited

```
X-Gly-His-Lys-Y (I)    (SEQ ID NO. 8-9)
``` or their conjugates corresponding to the general formula (II)

```
A-X-Gly-His-Lys-Y (II)    (SEQ ID NO. 10-11)
``` in which
A is such as defined above,
X represents a chain of 1 to 3 Lys residues, possibly methylated or, in the case of the formula (II), a bond,
Y represents an —OH or —NH2 group,
or A-X represents a hydrogen atom,
in the form of enantiomers or diastereomers, as well as their mixtures, including racemic mixtures and complexes with zinc which can be formed with these peptides or peptide conjugates.

The cosmetic compounds according to the present invention, intended for topical application to the scalp, can in addition include a UVB filter enabling photoprotection of the scalp. Thus, among adapted UVB filters can be cited, using their INCI names:
P-aminobenzoic acid or PABA and its esters:
  Ethylhexyl dimethyl PABA
  PEG-25 PABA
The cinnamates:
  Ethylhexyl methoxycinnamate
  Isoamyl p-methoxycinnamate
  Octocrylene
The salicylates:
  Homosalate
  Ethylhexyl salicylate The benzimidazoles:
   Phenylbenzimidazole sulfonic acid
The benzylidene camphor derivatives:
   4-Methylbenzylidene camphor
   Benzylidene camphor
   Camphor benzalkonium methosulfate
   Polyacrylamidomethyl benzylidene camphor
The triazines:
   Ethylhexyl triazone
   Diethylhexyl butamido triazone.

The peptides of the invention have been the object of pharmacological tests which make it possible to demonstrate their anti-hair-loss activity.

The Effects of Various Peptides on the Growth of Mouse Vibrissae In Vitro

In order to demonstrate the stimulatory effect of thymopoietin peptide derivatives on hair growth, anagen-phase mouse vibrissae hair follicles were placed in culture according to the technique described by Philpott (Philpott et al., 1994. *Human hair growth in vitro: a model for the study of hair biology*. Journal of dermatological science 7: S55-S72) in the presence or absence of thymopoietin peptide derivatives. The growth of the hair shaft of these hair follicles was followed for several days (Day 0 to Day 4). The results are reported in the table below for peptides 1- and 2-described above, for which A is acetic acid. These results show that these peptides stimulate hair growth when the hair follicles are kept alive in vitro.

|  | Control | Peptide 1- $10^{-7}$ M | Peptide 2- $10^{-7}$ M |
|---|---|---|---|
| Day 0 | 0.00 | 0.00 | 0.00 |
| Day 1 | 0.27 | 0.90 | 0.83 |
| Day 2 | 0.43 | 1.38 | 1.46 |
| Day 3 | 0.55 | 1.86 | 1.62 |
| Day 4 | 0.55 | 1.87 | 1.62 |

The following formulation examples illustrate the present invention.

EXAMPLE 1

A Lotion that Includes the Peptide Conjugate Ac-Lys-Asp-Val-DOPA-NH2(SEQ ID NO: 6)

|  | (in g) |
|---|---|
| Peptide Ac-Lys-Asp-Val-DOPA-NH2 (SEQ ID NO: 6) | $5 \cdot 10^{-6}$ |
| 95° ethanol | 60 |
| Propylene glycol | 10 |
| Water - preservatives - fragrance | qsp 100— |

EXAMPLE 2

A Lotion that Includes the Peptide Conjugate Ac-Arg-Lys-Asp-Val-HomoPhe-NH2(SEQ ID NO: 5)

|  | (in g) |
|---|---|
| Peptide Ac-Arg-Lys-Asp-Val-HomoPhe-NH2 (SEQ ID NO: 5) | $10^{-5}$ |
| Water | 81 |
| Keltrol T | 0.5 |
| Techpolymer MB-4C | 1 |
| Sepigel 305 | 0.5 |
| Silicone oil 0.2 1401 | 2 |
| Butylene glycol | 5— |

The invention claimed is:

1. A peptide corresponding to the formula (I)

W-Lys-Asp-Val-Z (I)  (SEQ ID NO. 1-2)

or its peptide conjugate corresponding to the formula (II)

A-W-Lys-Asp-Val-Z (II)  (SEQ ID NO. 3-4)

in which A represents the radical corresponding to a monocarboxylic acid of general formula (III)

HOOC—R     (III)

in which R represents a C1-C24 aliphatic radical, linear or branched, possibly substituted by a hydroxy group, capable of including one or more unsaturations, lipoic acid or its reduced form, dihydrolipoic acid, N-lipoyl-lysine, or retinoic acid, and W represents Glu-Gln-Arg, Arg-Lys, Arg-Lys-Asp, Arg or a bond, when Z represents Tyr-Val-Gln-Leu-Tyr-NH$_2$ (SEQ ID NO:12), Leu-DOPA, DOPA-NH$_2$, or HomoPhe-NH$_2$, or W represents Gly-Gln-Gln or Glu-Gln, when Z represents Tyr-Val-Gln-Leu-Tyr-NH$_2$ (SEQ ID NO:12), Leu-DOPA, Val-Tyr-OH, Val-Tyr-NH$_2$, Tyr-NH$_2$, Tyr-OH, DOPA-NH$_2$, or HomoPhe-NH$_2$, in the form of enantiomers or diastereomers, as well as their mixtures, including racemic mixtures, the peptide of formula (I) and the peptide conjugate of formula (II) which can be present in the form of complexes with zinc.

2. The peptide or peptide conjugate according to claim 1, wherein the acid of general formula (III) is an omega-3 acid selected from the group consisting of: α-linolenic acid, cervonic acid, timnodonic acid, and pinolenic acid, or an aliphatic C1-C24 radical selected from the group consisting of: acetic acid, myristic acid, palmitic acid hydroxydecenoic and decenoic acids, or an acid selected from the group consisting of: lipoic acid, the reduced form of lipoic acid, dihydrolipoic acid, N-lipoyl-lysine, and retinoic acid.

3. The peptide or conjugate according to claim 2, wherein A is lipoic acid or acetic acid.

4. The peptide conjugate according to claim 1, wherein said peptide conjugate is selected from the group consisting of:

1- A-Arg-Lys-Asp-Val-DHomoPhe-NH2

2- A-Arg-Lys-Asp-Val-HomoPhe-NH2    (SEQ ID NO. 5)

3- A-Lys-Asp-Val-DOPA-NH2           (SEQ ID NO. 6)

4- A-DLys-Asp-Val-DOPA-NH$_2$, and

5- A-Arg-Lys-Asp-Val-DOPA-NH2       (SEQ ID NO. 7), wherein A is an acid of formula (III) as defined in claim 1.

5. A cosmetic or pharmaceutical compound comprising the peptide or the conjugate according to claim 1.

6. A method of stimulating hair growth which comprises administering an effective amount of the peptide or the peptide conjugate according to claim 1 to a patient in need thereof.

7. The cosmetic compound according to claim 5, wherein the cosmetic compound further comprises a compound selected from the group consisting of: minoxidil, nicotinic acid esters, anti-inflammatory agents, retinoic acid and derivatives thereof, retinol, and 5α-reductase inhibitors.

8. The cosmetic compound according to claim 5, further comprising a peptide corresponding to the formula (I)

X-Gly-His-Lys-Y (I)  (SEQ ID NO. 8-9)

or conjugates thereof corresponding to the formula (II)

A-X-Gly-His-Lys-Y (II)  (SEQ ID NO. 10-11)

wherein A is such as defined in claim 1, X represents a chain of 1 to 3 Lys residues, possibly methylated or, in the case of the formula (II), a bond, Y represents an —OH or —NH2 group, or A-X represents a hydrogen atom, in the form of enantiomers of diastereomers, and mixtures thereof, including racemic mixtures and complexes with zinc.

9. The cosmetic compound according to claim 5, wherein said cosmetic compound further comprises a UVB filter selected from the group consisting of: P-aminobenzoic acid and PABA and esters thereof including cinnamates, salicylates, benzimidazoles, benzylidene camphor derivatives and triazines.

10. A cosmetic treatment method of decreasing hair loss which comprises applying on a scalp of a patient in need thereof the cosmetic compound according to claim 5.

11. A food supplement comprising the peptide or the peptide conjugate according to claim 1.

12. A cosmetic treatment method of decreasing hair loss which comprises the peptide or the peptide conjugates according to claim 1.

13. The food supplement according to claim 11, further comprising one or more of the compounds that improves hair growth according to claim 7 or claim 8.

14. The method according to claim 12, wherein said food supplement further comprises one or more of the compounds that improves hair growth according to claim 7 or claim 8.

* * * * *